United States Patent
Farzin

(10) Patent No.: US 9,480,605 B2
(45) Date of Patent: Nov. 1, 2016

(54) DEVICE FOR EXTRACTING DRIED NASAL MUCUS OR EARWAX

(71) Applicant: Nina D. Farzin, Potomac, MD (US)

(72) Inventor: Nina D. Farzin, Potomac, MD (US)

( * ) Notice: Subject to any disclaimer, the term of this patent is extended or adjusted under 35 U.S.C. 154(b) by 194 days.

(21) Appl. No.: 14/072,123

(22) Filed: Nov. 5, 2013

(65) Prior Publication Data

US 2015/0127036 A1    May 7, 2015

(51) Int. Cl.
*A61F 11/00* (2006.01)
*A61B 17/24* (2006.01)

(52) U.S. Cl.
CPC ........ *A61F 11/006* (2013.01); *A61B 2017/246* (2013.01)

(58) Field of Classification Search
CPC ........... A61F 11/006; A61B 2017/246; A61B 17/24; A61B 10/02; A61B 17/320708
See application file for complete search history.

(56) References Cited

U.S. PATENT DOCUMENTS

| D277,880 S | 3/1985 | Paczko |
| D335,927 S | 5/1993 | Burgio et al. |
| 5,334,212 A | 8/1994 | Karell |
| 5,649,942 A * | 7/1997 | Yeh ........................ A61B 17/50 606/160 |
| 5,715,850 A | 2/1998 | Markgraaf |
| 5,888,199 A * | 3/1999 | Karell ................... A61F 11/006 606/162 |
| D423,669 S | 4/2000 | Huttner et al. |
| D439,338 S | 3/2001 | Huttner et al. |
| D444,556 S | 7/2001 | Estrem |
| D447,237 S | 8/2001 | Huttner et al. |
| 6,270,510 B1 | 8/2001 | Westendorf |

(Continued)

FOREIGN PATENT DOCUMENTS

| EP | 1138292 A1 | 10/2001 |
| WO | WO-2010140144 A1 | 12/2010 |

OTHER PUBLICATIONS

International Search Report Form PCT/ISA/220, Application No. PCT/US2014/063363, date of mailing: Jan. 30, 2015, 14 pages.

(Continued)

*Primary Examiner* — Thomas McEvoy
(74) *Attorney, Agent, or Firm* — The Law Office of Patrick F. O'Reilly III, LLC

(57) ABSTRACT

A device for removing mucus (dried or wet) from a nostril of a subject or for removing earwax (dry or wet) from an ear canal of a subject includes a handle portion or grip portion to facilitate manipulation of the device, at least one of a bowl or a loop at an end of the handle portion, and a stop located between the handle portion and the bowl or loop. The bowl or loop is sized and configured for insertion into a nostril or an ear canal of the subject, and the stop is sized to prevent insertion of the stop into the nostril or ear canal and to limit the extent that the bowl or loop can be inserted into the nostril or ear canal, thereby reducing or eliminating the potential for accidental injury or extreme discomfort to the subject during use.

21 Claims, 2 Drawing Sheets

(56) References Cited

U.S. PATENT DOCUMENTS

| | | |
|---|---|---|
| D470,238 S | 2/2003 | Boggs |
| D490,523 S | 5/2004 | Samborski |
| D525,365 S | 7/2006 | Mills |
| D539,426 S | 3/2007 | Callaghan |
| D567,373 S | 4/2008 | Irby |
| D583,045 S | 12/2008 | Leal |
| D631,957 S | 2/2011 | Perez et al. |
| D652,925 S | 1/2012 | Nanda |
| 2006/0085018 A1* | 4/2006 | Clevenger .................. 606/162 |
| 2008/0142385 A1* | 6/2008 | Stein et al. .................. 206/362 |
| 2009/0300867 A1 | 12/2009 | Farhoudi |
| 2011/0066172 A1* | 3/2011 | Silverstein .................. 606/162 |
| 2012/0283616 A1 | 11/2012 | Edme et al. |

OTHER PUBLICATIONS

First office action on the merits (Non-Final Rejection) in U.S. Appl. No. 29/453,288, mailed on Aug. 14, 2015.

* cited by examiner

DEVICE FOR EXTRACTING DRIED NASAL MUCUS OR EARWAX

CROSS-REFERENCE TO RELATED APPLICATIONS

Not Applicable

FIELD OF THE DISCLOSURE

This disclosure relates to a device for removing a material from a nostril or ear canal.

BACKGROUND OF THE DISCLOSURE

The accumulation of dried nasal mucus in the nostrils can make breathing difficult. Additionally, it is believed by many that excess mucus and debris should be removed from the nostrils and sinus passages to promote health and relieve or decrease symptoms associated with rhinitis or sinusitis, including facial pain, headache, halitosis, cough, anterior rhinorrhea and nasal congestion.

A known technique for cleansing or removing excess mucus and debris from the nostrils is nasal irrigation (also known as nasal lavage or nasal douche), which is a personal hygiene practice involving flushing the nasal cavity with water or a saline solution, and encompasses pouring the solution from a container into one nostril and allowing it to run out the other nostril and into a sink or spraying the solution into the nostrils. Nasal irrigation techniques can be difficult, uncomfortable and messy.

Other known techniques have generally involved removing mucous (wet or dry) from the nostrils with a finger or a cotton swab or similar device. Use of a finger to remove mucous (wet or dry) is often ineffective and is generally shunned as a disgusting practice. Use of devices such as cotton swabs can also be ineffective and could result in injury and/or extreme discomfort. The use of a finger, cotton swabs or other known devices for removing mucus can actually push the mucus up the nostril, increasing discomfort and/or exacerbating breathing difficulties. These devices and techniques are especially unsuitable for infants and children because of the smaller size (e.g., diameter) of their nostrils, which prevents fingers or other objects from being used to remove mucus. Further, it can be dangerous to insert fingers or other known devices into nostrils of subjects, especially infants and small children.

Expelling mucus by forcefully exhaling through the nostrils ("blowing one's nose") is generally ineffective at removing dried mucus material.

Nasal aspirators for evacuating mucus is somewhat effective for removing wet mucus from the nostrils, but is generally incapable of removing dried mucus, especially mucus encrusted on nasal tissue.

None of the afore-mentioned techniques or devices is well suited for removing dried mucus (also known as "boogers") from nostrils. The afore-mentioned techniques are particularly unsuitable for removing dried mucus from the nostrils of infants.

SUMMARY OF THE DISCLOSURE

In certain disclosed embodiments, a device for removing mucus from a nostril or earwax from an ear canal includes a handle portion and an extraction portion at an end of the handle portion, wherein the extraction portion includes a bowl or a loop, and a stop located at an end of the handle portion that is adjacent the bowl or loop. The bowl or loop is configured for extracting mucus or earwax and is sized to fit within a nostril or an ear canal. The stop is sized to prevent insertion of the stop into the nostril or ear canal and limit the depth that the bowl or loop can be inserted into the nostril or ear canal.

In certain embodiments, the bowl and loop can be sized especially for infants.

In certain disclosed embodiments, the device includes an extraction portion at each of opposite ends of the handle portion, wherein one extraction portion is a bowl and the other is a loop.

These and other features, advantages and objects of the various embodiments will be better understood with reference to the following drawings, specification and claims.

DESCRIPTION OF THE ILLUSTRATED EMBODIMENT(S)

A device 10 for removing mucus from a nostril or earwax from an ear canal is shown in FIGS. 1-5. Device 10 includes a handle portion 12 or grip portion that facilitates manipulation of the device, a first extraction portion 14, and a second extraction portion 16.

Figure 1:
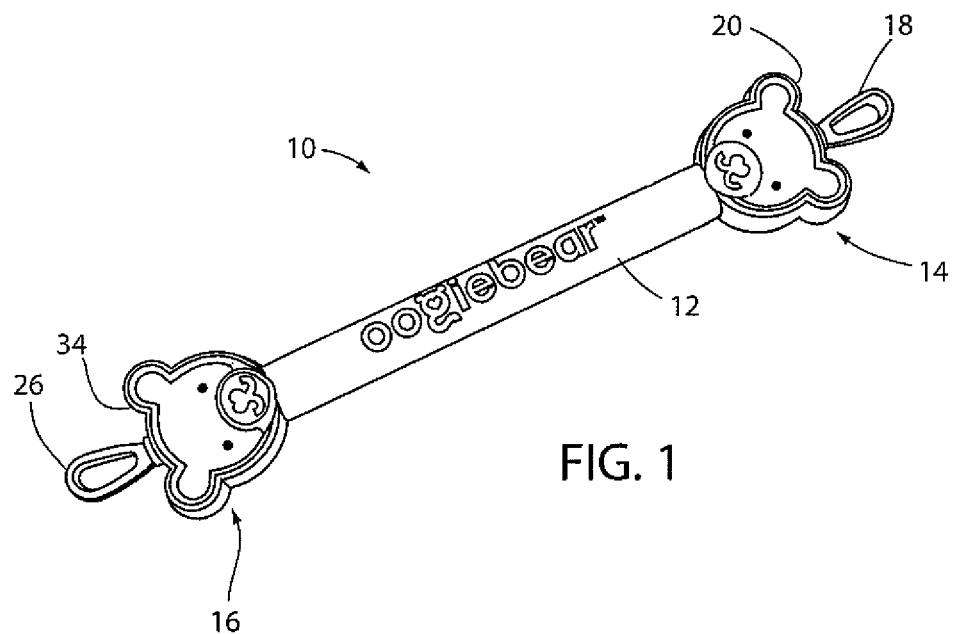
FIG. 1 is a perspective view of a device for removing mucus from a nostril or earwax from an ear canal.
Figure 2:
FIG. 2 is a top view of the device shown in FIG. 1.
Figure 3:
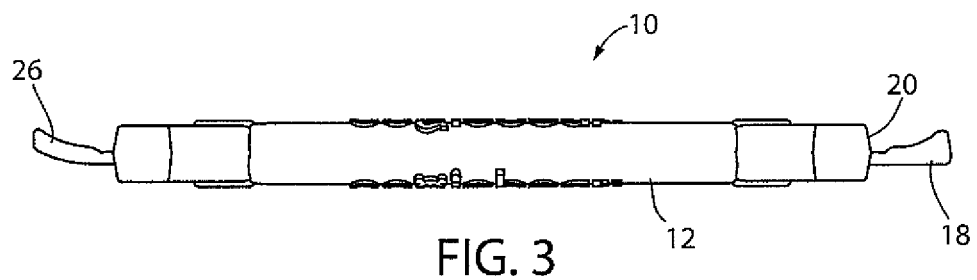
FIG. 3 is a side view of the device shown in FIG. 1.
Figure 4:
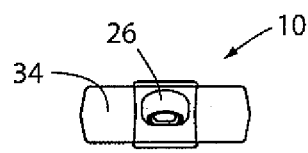
FIG. 4 is a first end view of the device shown in FIG. 1.
Figure 5:
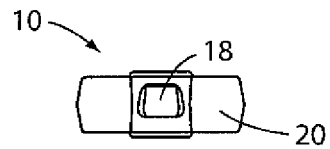
FIG. 5 is an opposite second end view of the device shown in FIG. 1.

Extraction portion 14 includes a bowl 18 having sidewalls 22 and a bottom 24 (FIG. 2). Bowl 18 is configured to allow earwax to be removed from an ear canal or allow mucus to be removed from a nostril using a scooping action. Bowl 18 is particularly useful for removing dried mucus from the nostrils or dried earwax from the ear canals.

Extraction portion 16 includes a loop 26 that defines an opening or hole 28. Loop 26 is configured to allow extraction of earwax from an ear canal or mucus from a nostril, and is particularly useful for removing gooey or wet mucus (i.e., mucus having sufficient moisture content to exhibit at least some fluid properties, such as the ability to flow when stressed) from the nostrils and wet earwax from the ear canals.

Located between handle portion 12 and bowl 18 at an end of handle portion 12 is a first stop 20 that has a width perpendicular to the length of handle portion 12 and the direction of insertion of bowl 18 into an ear canal or nostril that prevents insertion of stop 20 into the nostril or ear canal into which bowl 18 is inserted and limits the depth that bowl 18 can be inserted into the nostril or ear canal.

A suitable length of the bowl 18, measured from stop 20 to the distal end of bowl 18 is from about 5 mm to about 10 mm. This is a length that can effectively reach most mucus in the nostril or earwax in an ear canal, while preventing injury or extreme discomfort through overly deep penetration into the nostrils or ear canals. Typically, the width of bowl 18 is less than the length, with a suitable width (the largest dimension perpendicular to the length direction) of bowl 18 being from about 3 mm to about 10 mm. The length of bowl 18 is typically from about 100% to 300% of the width of bowl 18 (i.e., from about equal to the width to about three times the width of the bowl). The depth of bowl 18 can be about equal to the width or less than the width of bowl 18 (e.g., about 2 mm to about 5 mm).

Stop 20 is sized and configured to prevent stop 20 from being inserted into the nostrils or ear canals. In the illustrated embodiment, stop 20 presents a broad relatively flat stop surface 20 (FIG. 5) that engages exterior portions of the nose or ear of a subject on which the device 10 is used to prevent over insertion of bowl 18 into the nostril or ear canal of the subject. Suitable dimensions for stop surface 20 are from about 12 mm to about 20 mm wide by from about 3 mm to about 10 mm in depth. Typically, stop surface 20 has a generally rectangular, flat surface, the illustrated embodiment deviating only slightly to accommodate the shape of the top of the decorative teddy-bear head design.

The illustrated handle portion 12 is an elongate member having a generally rectangular profile that is of length, width and thickness that comfortably facilitates gripping of the device 10 during use. Other types of handle or grip portions can be used if desired. The length of handle portion 12 can be from about 3 cm to about 10 cm, although a handle portion shorter than 3 cm or longer than 10 cm would also be expected to perform adequately. The length of the handle portion (the distance from the proximal end of the handle portion to the stop surface 32 at the opposite or distal end of the handle portion, or the distance between two stop surfaces at opposite ends of the device) is typically at least 200% of the length of the extraction portion (e.g., the length of bowl 18).

In the illustrated device 10, the ends of the handle portion 12 are provided with ornamental features that resemble the head of a "teddy bear," with the top of the head forming stop surface 20. However, various other ornamental features may be used. Alternatively, a flat stop surface without any ornamentation can be used.

The other end of device 10 opposite bowl 18 has a second extraction portion 16 that includes a loop 26 defining an opening 28, and a stop 34. Loop 26 is capable of more easily extracting wet or slimy mucus or earwax than bowl 18, whereas bowl 18 is capable of more easily extracting dry mucus or earwax than loop 26. Thus, by providing two different types of extraction means (bowl 18 and loop 26), easier removal of a wider variety of mucus and earwax materials is facilitated.

The dimensional characteristics (width, length and depth) of loop 26 and stop 34 are the same or substantially the same as those for bowl 18 and stop 20.

Figure 6:
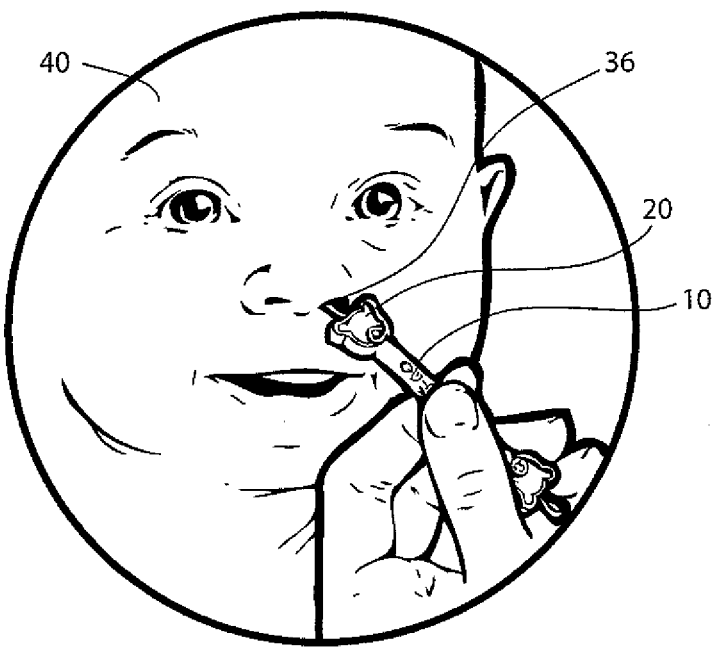
FIG. 6 is an illustration of the device shown in FIG. 1 being used to extract mucus from a nostril of an infant.

FIG. 6 shows device 10 being used to remove mucus from nostril 36 of infant 40. Stop 20 or 34 prevents bowl 18 or loop 26 from accidently being inserted too deeply into nostril 36 of infant 40.

Figure 7:
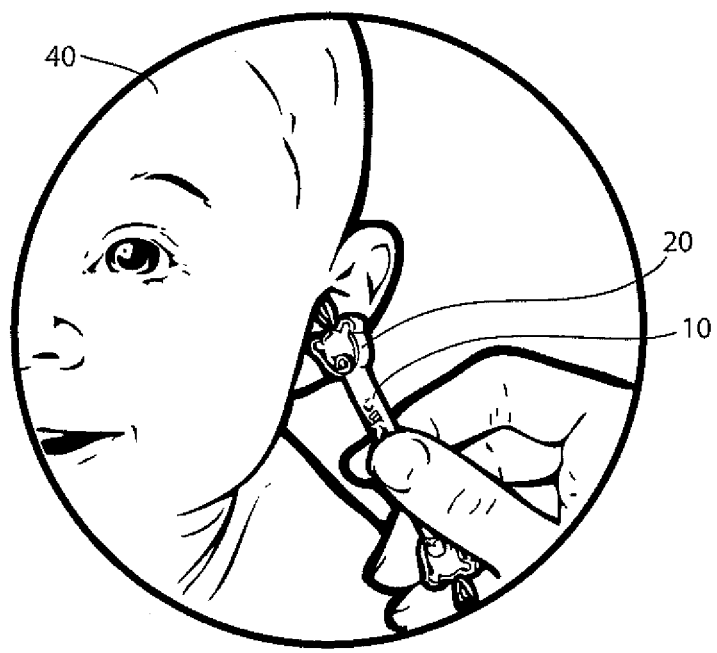
FIG. 7 is an illustration of the device shown in FIG. 1 being used to extract earwax from an ear canal of an infant.

FIG. 7 shows device 10 being used to remove earwax from an ear canal of infant 40. Stop 20 or 34 prevents bowl 18 or loop 26 from accidently being inserted too deeply into the ear canal of infant 40.

In a particular embodiment suitable for removing mucus from the nostrils of infants, the device has an overall length of about 90 mm, a length from one stop surface to the stop surface at an opposite end of about 75 mm. The stop surfaces have a width of about 17 mm and a depth of about 6 mm. The bowl has a length of about 8 mm, a width of about 5 mm, and a depth that varies along the length from about 1 mm near the stop surface to about 3 mm at the distal end. The loop has a length of about 5 mm, a width of about 5 mm and a depth that varies along the length of the loop from about 1 mm near the stop surface to about 2 mm at the distal end. The opening in the loop has a generally tear-drop shape, with a length that is about 5 mm and a width that is about 2 mm. Each of the stops have a teddy bear face design or shape that is about 15 mm in the length direction of the device and a rod portion between the stops having a generally square or rectangular cross sectional shape with rounded corners, the width being about 6 mm and the thickness being about 6 mm. The device is comprised of a polypropylene core having a thickness and width that is about 2.4 mm between the stop surfaces and generally about 1 mm thick at the bowl and loop ends, and a thermoplastic elastomer (e.g., Versaflex™ CL E85) coating disposed over surfaces of the core.

Device 10 is made of soft rubber material, such as a silicone rubber or a thermoplastic elastomer (TPE) such as a styrenic block copolymer (TPE-s), polyolefin blends (TPE-o), elastomeric alloys (TPE-v or TPV), thermoplastic polyurethanes (TPU), and can have a Shore A hardness that is less than 100, less than 90, such as 50 to 100, 70-100 or 70-90. The rubber material should be free of any toxic or otherwise harmful or hazardous materials, such as phthalates or other plasticizers, that could be leached out during use. As an alternative device 10 can be made with an inner material that is more rigid (e.g., a polypropylene material having a Shore A hardness of about 100) and a softer rubber coating material (e.g., a TPE), such as Versaflex™ CL E85, a proprietary, plasticizer-free TPE having a Shore A hardness of about 85, available from GLS Thermoplastic Elastomers, a business unit of Polyone Corporation, Avon Lake, Ohio.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. A device for removing mucus from a nostril or earwax from an ear canal, comprising:
   a handle portion; and
   a first extraction portion at a first handle end of the handle portion, wherein the first extraction portion includes a bowl and a first stop located at the first handle end of the handle portion adjacent the bowl, the bowl sized and configured to fit within a nostril or an ear canal for extracting mucus or earwax, the bowl including a proximal wall, an oppositely disposed distal wall, a first sidewall having a first top edge and an oppositely disposed second sidewall having a second top edge, the second sidewall of the bowl being transversely spaced apart from the first sidewall of the bowl, the bowl further including a bottom wall extending from at least a portion of the first sidewall to at least a portion of the second sidewall, the bottom wall adjoining the portion of the first sidewall at a first corner and the bottom wall adjoining the portion of the second sidewall at a second corner, the first and second top edges of the respective first and second sidewalls being upwardly sloped from the proximal wall to the distal wall such that the distal wall extends to a higher elevation above the bottom wall than the proximal wall, the bowl being particularly configured to extract dry mucus or earwax using a scooping action, and the first stop sized to prevent insertion of the first stop into the nostril or ear canal and limit the depth that the bowl can be inserted into the nostril or ear canal.

2. The device of claim 1, in which the bowl has a length and a width, the length of the bowl being from about 100% to about 300% of the width of the bowl.

3. The device of claim 2, in which the first stop has a width that is at least 200% of the width of the bowl.

4. The device of claim 1, in which the handle portion is an elongate member having a length that is at least 200% of the length of the first extraction portion.

5. The device of claim 1, further comprising a second extraction portion at a second handle end of the handle portion, the second extraction portion including a loop and a second stop located at the second handle end of the handle portion adjacent the loop, the loop having a first loop end proximal to the second stop, an oppositely disposed second loop end distal from the second stop, and a bottom surface that is continuously upwardly tapered from the first loop end to the second loop end such that the second loop end of the loop is disposed at a higher elevation than the first loop end relative to a bottom surface of the handle portion, the loop being particularly configured to extract wet mucus or earwax, and the second stop having a stop surface with multiple curved portions facing the loop.

6. The device of claim 5, wherein the multiple curved portions of the stop surface comprise a central curved portion on which the loop is mounted, a first curved side portion disposed on a first side of the central curved portion, and a second curved side portion disposed on an opposite, second side of the central curved portion.

7. The device of claim 5, in which the loop has a length and a width, the length of the loop being from about 100% to about 300% of the width of the loop.

8. The device of claim 7, in which the second stop has a width that is at least 200% of the width of the loop.

9. The device of claim 1, in which the bowl has a length of from about 5 mm to about 10 mm, and a width of from about 3 mm to about 10 mm.

10. The device of claim 9, in which the first stop has a width that is at least 12 mm.

11. The device of claim 1 which is made of a rubber material having a Shore A hardness that is less than 100.

12. The device of claim 1, wherein the bottom wall of the bowl of the first extraction portion is generally flat.

13. A device for removing mucus from a nostril or earwax from an ear canal, comprising:
an elongate handle portion having opposite first and second handle ends;
a bowl extending from the first handle end, the bowl sized to fit within a nostril or an ear canal, the bowl including a proximal wall, an oppositely disposed distal wall, a first sidewall having a first top edge and an oppositely disposed second sidewall having a second top edge, the first sidewall of the bowl being transversely spaced apart from the second sidewall of the bowl, the bowl further including a bottom wall extending from at least a portion of the first sidewall to at least a portion of the second sidewall, the bottom wall adjoining the portion of the first sidewall at a first corner and the bottom wall adjoining the portion of the second sidewall at a second corner, the first and second top edges of the respective first and second sidewalls being upwardly sloped from the proximal wall to the distal wall such that the distal wall extends to a higher elevation above the bottom wall than the proximal wall, the bowl being particularly configured to extract dry mucus or earwax using a scooping action; and
a loop extending from the second handle end, the loop sized to fit within a nostril or an ear canal, the loop having a first loop end proximal to the second handle end, an oppositely disposed second loop end distal from the second handle end, and a bottom surface that is continuously upwardly tapered from the first loop end to the second loop end such that the second loop end is disposed at a higher elevation than the first loop end relative to a bottom surface of the elongate handle portion, the loop being particularly configured to extract wet mucus or earwax;
wherein, as a result of having both the bowl and the loop, the device is configured to effectively remove both the dry mucus or earwax and the wet mucus or earwax.

14. The device of claim 13, in which the bowl has a length and a width, the length of the bowl being from about 100% to about 300% of the width of the bowl.

15. The device of claim 13, in which the loop has a length and a width, the length of the loop being from about 100% to about 300% of the width of the loop.

16. The device of claim 13, in which the bowl has a length of from about 5 mm to about 10 mm, and a width of from about 3 mm to about 10 mm.

17. The device of claim 13 which is made of a rubber material having a Shore A hardness that is less than 100.

18. The device of claim 13, in which the loop has a length of from about 5 mm to about 10 mm, and a width of from about 3 mm to about 10 mm.

19. The device of claim 13, wherein the loop further comprises an opening disposed therethrough, the opening having a first opening end closer to a stop surface and an oppositely disposed second opening end further from the stop surface, and wherein an axial distance between a portion of the stop surface to which the loop is mounted and the first opening end of the opening is less than a width of the loop.

20. The device of claim 13, wherein the device has a two-part construction comprising an inner core formed from a first material and an outer cover disposed over the inner core and formed from a second material, the inner core extending into the bowl and the loop, and the first material having a Shore A hardness that is greater than a Shore A hardness of the second material.

21. The device of claim 20, wherein the first material forming the inner core comprises polypropylene and the second material forming the outer cover comprises a thermoplastic elastomer.

* * * * *